(12) United States Patent
Tata et al.

(10) Patent No.: US 11,696,671 B2
(45) Date of Patent: Jul. 11, 2023

(54) STEERABLE ENDOSCOPE WITH MOTION ALIGNMENT

(71) Applicant: Covidien AG, Neuhausen am Rheinfall (CH)

(72) Inventors: Derek Scot Tata, Loveland, CO (US); Alexandra Hause, Denver, CO (US); Peter Douglas Colin Inglis, Boulder, CO (US); Craig Allen Patton, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 45 days.

(21) Appl. No.: 16/995,181

(22) Filed: Aug. 17, 2020

(65) Prior Publication Data
US 2021/0052140 A1 Feb. 25, 2021

Related U.S. Application Data

(60) Provisional application No. 63/012,741, filed on Apr. 20, 2020, provisional application No. 62/888,906, filed on Aug. 19, 2019.

(51) Int. Cl.
*A61B 1/00* (2006.01)
*A61B 1/005* (2006.01)
*A61B 1/008* (2006.01)

(52) U.S. Cl.
CPC .......... *A61B 1/00006* (2013.01); *A61B 1/008* (2013.01); *A61B 1/00042* (2022.02);
(Continued)

(58) Field of Classification Search
CPC .............. A61B 1/0051; A61B 1/00039; A61B 1/00181; A61B 1/008; A61B 1/000094; A61B 1/00042; A61B 1/00097; A61B 5/7475; A61B 2034/2048; A61B 2034/2065; A61B 2034/301;
(Continued)

(56) References Cited

U.S. PATENT DOCUMENTS 8,194,122 B2 6/2012 Amling et al.
8,652,033 B2 2/2014 Berci et al.
(Continued)

FOREIGN PATENT DOCUMENTS

EP 2433553 A1 3/2012
JP 2014210085 A 11/2014

OTHER PUBLICATIONS

Siena, Francesco Luke, et al.; "The development of a novel steerable bougie to assist in airway management," Austrasian Medical Journal, 2016, vol. 9, No. 5, pp. 124-137. http://dx.doi.org/10.4066/AMJ.2016.2619.
(Continued)

*Primary Examiner* — Anh Tuan T Nguyen
*Assistant Examiner* — Sung Ham

(57) ABSTRACT

A steerable endoscope is provided with active steering control. An endoscope includes a flexible tubular body with first and second articulating segments, and a camera. In an embodiment, the endoscope includes an orientation sensor. A controller for the endoscope performs an automated analysis of an alignment between the motion axis of the endoscope and the viewing axis of the camera, and actively steers the endoscope to improve the alignment.

13 Claims, 10 Drawing Sheets

(52) U.S. Cl.
CPC ...... *A61B 1/0051* (2013.01); *A61B 1/000094* (2022.02); *A61B 1/00097* (2022.02); *A61B 1/00181* (2013.01)

(58) Field of Classification Search
CPC .......... A61B 2562/0219; A61B 1/0016; A61B 1/0052; A61B 1/05; A61B 5/067; A61B 5/6852; A61B 5/7425; A61B 1/00006
See application file for complete search history.

(56) References Cited

U.S. PATENT DOCUMENTS

| | | | |
|---|---|---|---|
| 8,715,172 B1 | 5/2014 | Girgis | |
| 8,746,239 B2 | 6/2014 | Yoshida | |
| 8,827,899 B2 | 9/2014 | Farr et al. | |
| 8,982,199 B2 | 3/2015 | Amling et al. | |
| 9,123,155 B2 | 9/2015 | Cunningham et al. | |
| 9,498,112 B1* | 11/2016 | Stewart | A61B 1/0676 |
| 9,538,908 B2 | 1/2017 | Allyn et al. | |
| 9,687,141 B2 | 6/2017 | McGrath | |
| 9,820,641 B2 | 11/2017 | McGrath | |
| 10,010,379 B1 | 7/2018 | Gibby et al. | |
| 10,149,957 B2 | 12/2018 | Runnels | |
| 2002/0062063 A1* | 5/2002 | Ogura | A61B 1/273 600/141 |
| 2007/0197896 A1 | 8/2007 | Moll et al. | |
| 2007/0236514 A1 | 10/2007 | Agusanto et al. | |
| 2008/0177146 A1 | 7/2008 | Chen | |
| 2008/0177148 A1 | 7/2008 | Chen et al. | |
| 2008/0312507 A1 | 12/2008 | Kim | |
| 2010/0168519 A1* | 7/2010 | Matsuo | A61B 1/0055 600/139 |
| 2011/0130632 A1 | 6/2011 | McGrail et al. | |
| 2011/0137127 A1 | 6/2011 | Schwartz | |
| 2011/0196199 A1* | 8/2011 | Donhowe | A61B 1/0051 600/102 |
| 2011/0245609 A1 | 10/2011 | Laser | |
| 2013/0057667 A1* | 3/2013 | McGrath | A61B 1/05 348/E7.085 |
| 2013/0096384 A1* | 4/2013 | Arai | G02B 23/2476 600/144 |
| 2013/0267838 A1 | 10/2013 | Fronk et al. | |
| 2014/0031700 A1* | 1/2014 | Ferrantelli | A61B 5/0077 600/407 |
| 2014/0121460 A1* | 5/2014 | Friedrich | A61B 1/0016 600/118 |
| 2014/0160261 A1 | 6/2014 | Miller et al. | |
| 2014/0275760 A1 | 9/2014 | Lee et al. | |
| 2014/0378763 A1* | 12/2014 | Atarot | A61B 1/00147 600/109 |
| 2015/0196228 A1* | 7/2015 | Akimoto | A61B 5/065 600/117 |
| 2016/0199009 A1* | 7/2016 | Gilboa | A61B 90/11 600/424 |
| 2016/0279365 A1 | 9/2016 | Esnouf | |
| 2017/0055809 A1* | 3/2017 | Omoto | A61B 1/0051 |
| 2018/0139392 A1* | 5/2018 | Rauniyar | A61B 90/37 |
| 2018/0192854 A1* | 7/2018 | Hata | A61B 1/00006 |
| 2018/0193102 A1 | 7/2018 | Inoue | |
| 2018/0292199 A1 | 10/2018 | Tojo et al. | |
| 2018/0296281 A1* | 10/2018 | Yeung | A61B 1/00009 |
| 2018/0303319 A1* | 10/2018 | Ikeda | A61B 1/0051 |
| 2018/0324352 A1* | 11/2018 | Furuhata | A61B 1/00009 |
| 2019/0133430 A1 | 5/2019 | Inglis et al. | |
| 2020/0121163 A1* | 4/2020 | Takahashi | A61B 1/0016 |
| 2021/0220594 A1* | 7/2021 | Biro | A61B 1/0052 |

OTHER PUBLICATIONS

Sowers, Nicholas, et al.; "Use of a flexible intubating scope in combination with a channeled video laryngoscope for managing a difficult airway in the emergency department," The Journal of Emergency Medicine, 2016, vol. 52, No. 2, pp. 315-319.http://dx.doi.org/10.1016/j.jermermed.2015.10.010.

Weissbrod, Philip A., et al.; "Reducing injury during video-assisted endotracheal intubation: The "smart stylet" concept," The Laryngoscope, Nov. 2011, vol. 121, pp. 2391-2393.

Rothfield, Kenneth; "The video laryngoscopy market: Past, present, and future," Anesthesiology News Guide to Airway Management, 2014, pp. 29-34.

Lee, Hyung-Chul, "Real-time endoscopic image orientation correction system using an accelerometer and gyrosensor," PLOS One | https://doi.org/10.1371/journal.pone.0186691 (Nov. 3, 2017).

Ambu_aScope_3_Large_Brochure_4963605 (Oct. 2017).

International Search Report and Written Opinion for PCT Application PCT/GB2018/053300 dated Feb. 20, 2019; 15 pgs.

International Search Report and Written Opinion for PCT/US2020/051734 dated May 14, 2020; 11 pgs.

PCT Invitation to Pay Fees, PCT Application No. PCT/EP2020/073196, dated Nov. 16, 2020.

* cited by examiner

STEERABLE ENDOSCOPE WITH MOTION ALIGNMENT

CROSS-REFERENCE TO RELATED APPLICATIONS

The present application claims priority to and the benefit of U.S. Provisional Application No. 62/888,906, filed on Aug. 19, 2019, and U.S. Provisional Application No. 63/012,741, filed on Apr. 20, 2020, the disclosures of which are incorporated by reference in their entirety for all purposes.

BACKGROUND

The present disclosure relates generally to medical devices and, more particularly, to steerable endoscopes with active motion alignment, and related methods and systems.

Medical endoscopes are long, flexible instruments that can be introduced into a cavity of a patient during a medical procedure in a variety of situations to facilitate visualization and/or medical procedures within the cavity. For example, one type of scope is an endoscope with a camera at its distal end. The endoscope can be inserted into a patient's mouth, throat, or other cavity to help visualize anatomical structures, or to facilitate procedures such as biopsies or ablations. The endoscope may include a steerable distal tip that can be actively controlled to bend or turn the distal tip in a desired direction, to obtain a desired view or to navigate through anatomy. However, these steerable scopes can be difficult to maneuver into the desired location and orientation within a patient's anatomy.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In an embodiment, a computer-controlled endoscope system includes an endoscope and a controller. The endoscope has a flexible tubular body with a first articulating segment at a distal end of the body, and a second articulating segment coupled to a proximal end of the first articulating segment. The first articulating segment includes a camera having a field of view along a camera axis and an orientation sensor sensitive to movement along a motion axis. The controller is in communication with the endoscope and has a hardware memory storing instructions for analyzing an alignment between the motion axis and the camera axis. The controller steers the first and second articulating segments of the endoscope during motion of the endoscope to improve the alignment.

In an embodiment, a method for computer-aided steering of an endoscope includes receiving, via a touch screen display, a user input to move a viewing axis of an endoscope. The endoscope has first and second independently articulating segments, a camera having a field of view along the viewing axis, and an orientation sensor. In response to the user input, the method includes articulating the first articulating segment of the endoscope to move the viewing axis. The method also includes receiving from the orientation sensor a motion signal indicating movement of the endoscope along a motion axis, comparing, at a processing chip, the motion axis with the viewing axis, and generating a steering signal that controls articulation of the first and second articulating segments to reduce a difference between the motion axis and the viewing axis.

In an embodiment, a computer-implemented method for automatic steering of an endoscope includes receiving, via a graphical user interface, a user input comprising a direction to move a viewing axis of an endoscope. The endoscope has first and second independently articulating segments, a camera having a field of view along the viewing axis, and an orientation sensor. The method includes generating a first steering signal with instructions for bending the first articulating segment of the endoscope in the direction indicated by the user input. The method also includes receiving from the orientation sensor a motion signal indicating forward motion of the endoscope, and generating a second steering signal with instructions for bending the second articulating segment during the forward motion of the endoscope in the absence of steering input from the user.

In an embodiment, a computer-controlled endoscope system includes an endoscope that includes a flexible tubular body having a first articulating segment at a distal end of the body and a second articulating segment proximal of the first articulating segment, wherein the first articulating segment includes a camera and an orientation sensor. The system also includes a controller in communication with the endoscope that receives a user steering input and a motion signal from the orientation sensor. The controller includes a steering controller that controls independent articulation of the first articulating segment and the second articulating segment to articulate the first articulating segment to assume an orientation of a camera axis of the camera according to the user steering input and to maintain the camera axis in the orientation during forward motion of the endoscope by articulating the first articulating segment and second articulating segment.

Features in one aspect or embodiment may be applied as features in any other aspect or embodiment, in any appropriate combination. For example, any one of system, laryngoscope, handle, controller, endoscope, or method features may be applied as any one or more other of system, laryngoscope, controller, endoscope, or method features.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

A medical scope or endoscope as provided herein is a thin, elongated, flexible instrument that can be inserted into a body cavity for exploration, imaging, biopsy, or other clinical treatments, including catheters, narrow tubular instruments, or other types of scopes or probes. Endoscopes may be navigated into the body cavity (such as a patient's airway, gastrointestinal tract, oral or nasal cavity, or other cavities or openings) and be steered into by the user via advancement of the distal end to a desired position and, in certain embodiments, biomimetic motion of the endoscope. Endoscopes may be tubular in shape.

Advancement of long, flexible medical devices into patient cavities is typically via force transferred from a proximal portion of the device (outside of the patient cavity), that results in advancement of the distal tip within the patient cavity. For example, a doctor or other caregiver holding a proximal portion (such as a handle) of the medical device outside of the patient cavity pushes downward or forward, and the resulting motion is transferred to the distal tip, causing the tip to move forward within the cavity. Similarly, a pulling force applied by the caregiver at the proximal portion may result in retreat of the distal tip or movement in an opposing direction out of the patient cavity. However, because patient cavities are not regularly shaped or sized, the endoscope moves through a tortuous path, and the transferred force in a pushing or pulling motion from the proximal end may not result in predictable motion at the distal tip.

Figure 1A:
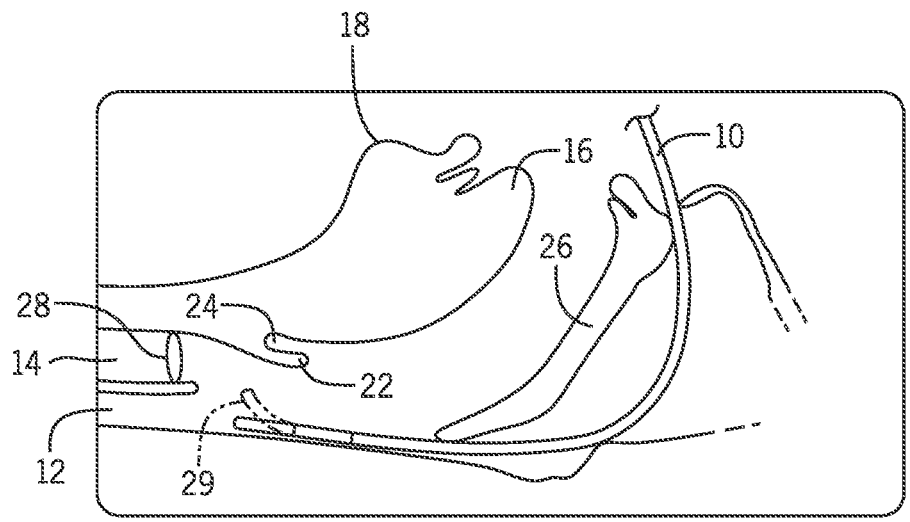
FIG. 1A is a cross-sectional view of an endoscope moving in a distal direction through a patient cavity.
Figure 1B:
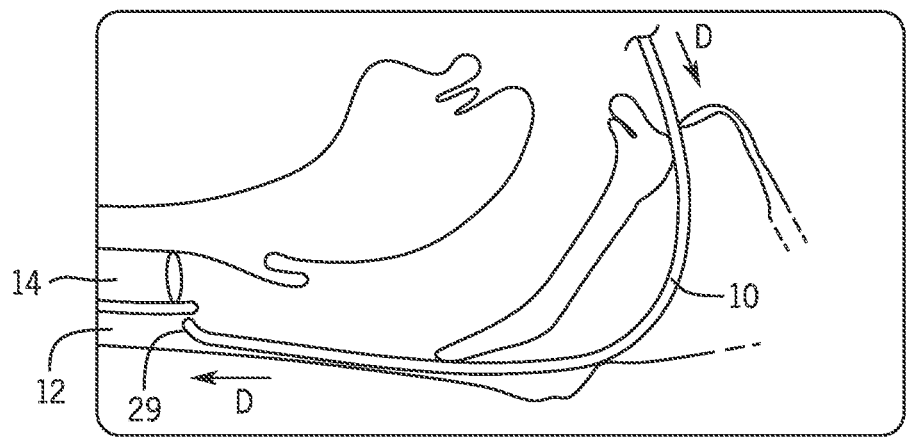
FIG. 1B is a cross-sectional view of an endoscope moving in a distal direction through a patient cavity.

An example of undesirable motion is shown in FIGS. 1A-B, which show cross-sectional views of an endoscope 10 moving in a distal direction through a patient cavity. In this example, the patient cavity is the nasal and oral cavities, leading to the esophagus 12 and trachea 14, and the operator intends to guide the endoscope 10 into the trachea 14. Also labeled for reference are the patient's tongue 16, chin 18, vocal cords 28, and palate 26. In FIG. 1A, the operator has moved the endoscope 10 forward through the nasal cavity to the area behind the epiglottis 22 and vallecula 24. At this point, the operator stops and bends the distal tip 29 of the endoscope upward (in the figure) toward the trachea 14, as indicated by the dotted lines of the distal tip of the endoscope 12. The distal tip 29 can be articulated into this upward bend in order to allow the operator to control the view of the camera at the distal tip 29 and look around inside the patient cavity.

The trachea is above (anterior, toward the patient's chest) the esophagus, and thus the endoscope must navigate in an anterior direction to avoid entry into the esophagus. In FIG. 1B, the operator pushes the endoscope 10 forward, in the distal direction, as indicated by arrows D. However, the forward motion of the endoscope moves it forward into the esophagus 12, rather than the trachea 14. If the operator is intending to intubate the patient (pass an endotracheal tube into the patient's trachea), this movement of the endoscope is undesirable. In fact, if the operator does not recognize that the endoscope has moved into the esophagus instead of the trachea, the operator could inadvertently perform an esophageal intubation (inserting the endotracheal tube into the esophagus, rather than the trachea), which can cause a medical emergency for the patient (as breathing gases are then delivered into the gastrointestinal system, instead of into the lungs).

FIGS. 1A-B demonstrate a pushing force at the proximal end of the endoscope (outside of the patient) may be insufficient to cause the distal tip 29 to steer in a desired direction inside the patient cavity. Smoothly navigating a length of the endoscope 10 through curved or irregular portions of a patient cavity can be particularly challenging.

Provided herein is an articulating endoscope with computer-controlled or automatically-controlled steering that aligns the endoscope's motion with its direction of view. This alignment may be performed to correct, refine, or augment user-provided steering inputs that provide rough guidance as to a desired position of the distal end. According to an embodiment, an endoscope system includes an endoscope with a flexible tubular body including first and second articulating segments at its distal end. The first articulating segment includes a camera having a field of view along a camera axis, and an orientation sensor sensitive to motion along a motion axis. The system also includes a controller in communication with the endoscope, and the controller performs automated analysis of an alignment between the motion axis and the camera axis. The controller actively steers the first and second segments of the endoscope to improve the alignment. While embodiments are disclosed in the context of first and second articulating segments, it should be understood that the endoscope system may include an endoscope with additional articulating segments (ex., third, fourth) as provided herein.

FIGS. 2A-D show cross-sectional views of an endoscope 220 positioned within and moving through a patient cavity, according to an embodiment of the present disclosure. The endoscope 220 includes a camera 230 at a distal tip 229 of the endoscope 220. The depicted motion pattern includes articulation of different (e.g., first, second) actuatable portions of a steerable endoscope 220 to create a desired movement through the patient's trachea. The nasal and oral cavities and trachea are shown by way of example, and in other embodiments, the endoscope may be passed into other patient cavities, and through other variations in anatomy.

FIGS. 2A-D show a rectangular cross-sectional view of the endoscope 220 moving through the patient anatomy, as well as a circular field of view 230V showing the view from the camera 230 of the endoscope 220. The endoscope 220 includes two steerable segments 232, 234 at the distal region of the endoscope 220. The two steerable segments are coupled to each other, with the first segment 232 distal of the second 234. Each segment 232, 234 can articulate independently of the other segment. In an embodiment, the segments 232, 234 may be directly adjacent to one another or may be separated by an intervening, connecting portion of the endoscope 220. In an embodiment, each segment 232, 234 can bend and curve in three dimensions (not just in a single plane, such as up/down or right/left), curving to point in all directions, up to a limit of its range of motion. For example, in an embodiment each segment can bend up to 90 degrees in any direction, enabling it to move within a hemisphere having a radius equal to the segment's length. Each segment is manipulated by an actuation system, including one or more actuators (such as sleeved pull-wires or other actuators described below), which move to bend or un-bend the segment into or out of a curved shape. Each segment 232, 234 may be controlled by a central actuation system that controls all articulating segments or may be coupled to a dedicated actuation system for each articulating segment.

Figure 2A:
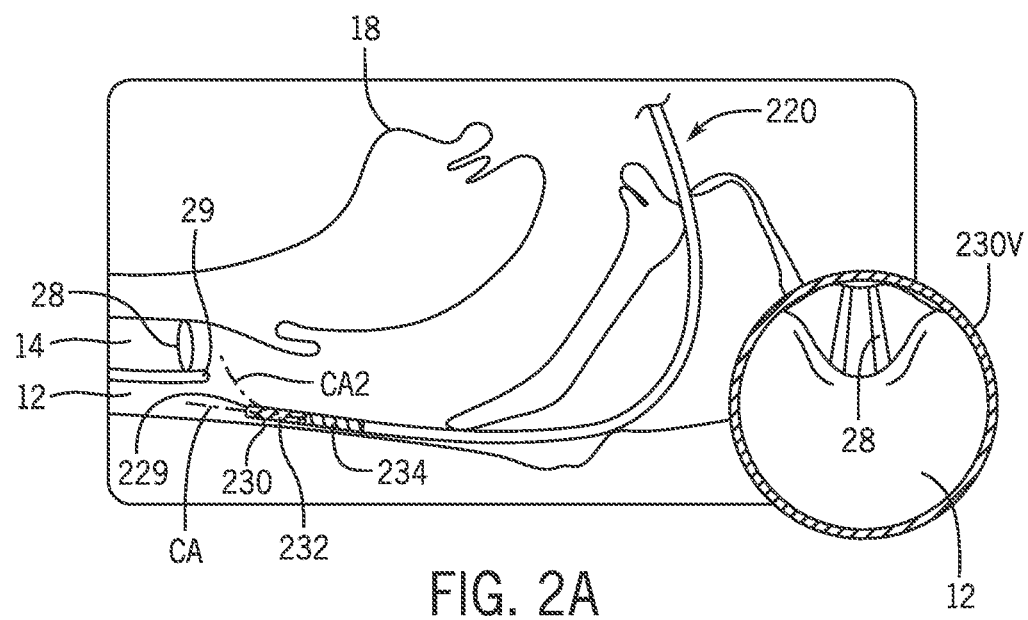
FIG. 2A is a cross-sectional view of an articulating endoscope with active motion alignment, according to embodiments of the present disclosure.

In FIG. 2A, the two steerable segments 232, 234 are in a resting, default position, in which they are not being actively bent. The endoscope 220 has passed through the patient's nasal cavity into the throat, and is pointed toward the patient's esophagus 12. The camera 230 is pointed along a camera axis CA, as indicated by the dashed line. In this configuration, with the segments 232, 234 straight, the axis CA points toward the patient's esophagus 12. The camera's view 230V shows the view of the esophagus 12, with the vocal cords 28 visible toward the top of the view.

Still referring to FIG. 2A, the caregiver can provide an input (e.g., a user input) to steer the camera up toward the vocal cords 28. For example, the caregiver can tap on the vocal cords 28 on the field of view 230V displayed on a touch screen, to command the endoscope to bend upward toward that view. The user's touch input indicates that the direction CA2 is where the user wants the camera to point. In response, the endoscope bends the first segment 230 upward, as shown by the second dashed line CA2 in FIG. 2A.

Figure 2B:
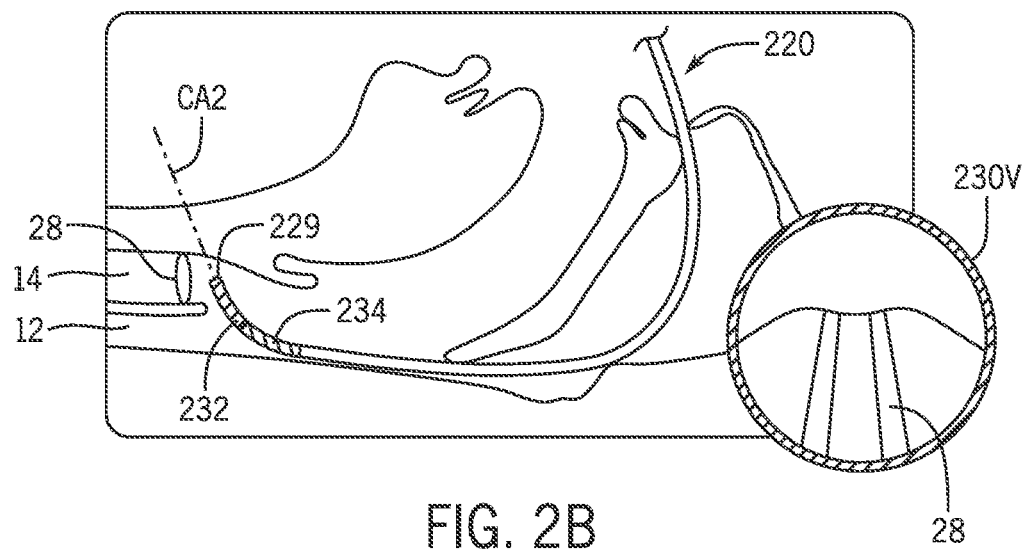
FIG. 2B is a cross-sectional view of an articulating endoscope with active motion alignment, according to embodiments of the present disclosure.
Figure 2C:
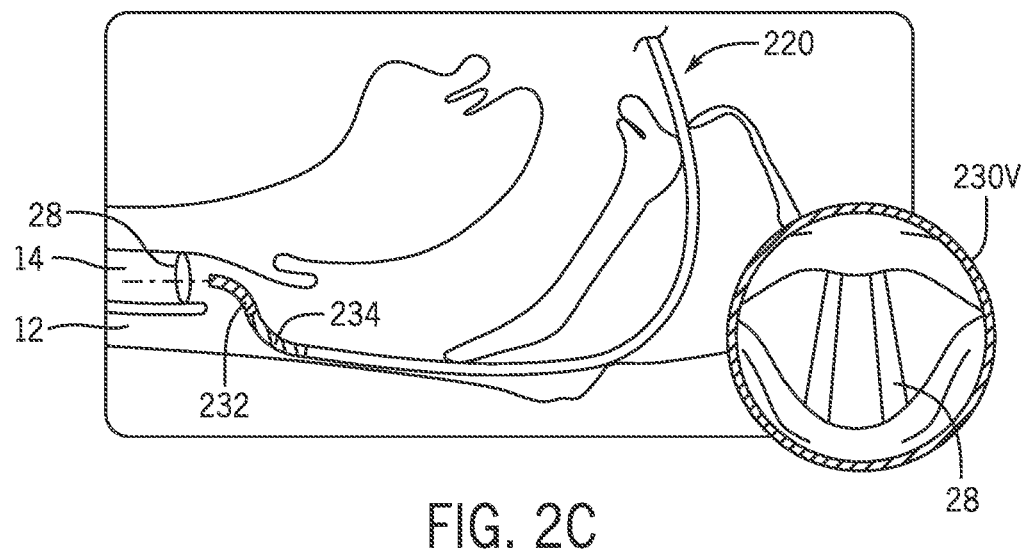
FIG. 2C is a cross-sectional view of an articulating endoscope with active motion alignment, according to embodiments of the present disclosure.
Figure 2D:
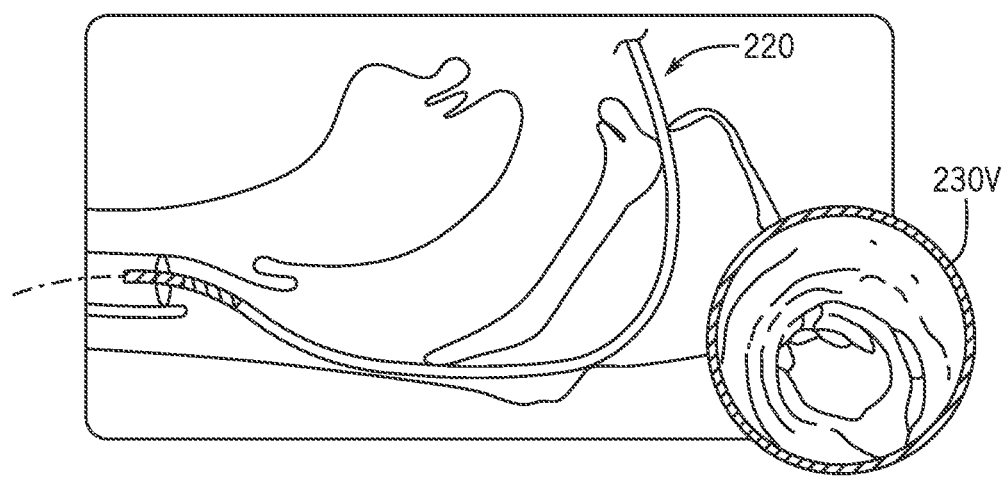
FIG. 2D is a cross-sectional view of an articulating endoscope with active motion alignment, according to embodiments of the present disclosure.

After steering, the endoscope is now curved along segment 232 to point along axis CA2, as shown in FIG. 2B. At this point, if the endoscope moves forward in a distal direction, without any further steering, it may hit the tracheal wall 29, or pass underneath that into the esophagus 12. Accordingly, in an embodiment, the endoscope 220 actively steers itself to align its motion with the camera axis. This automatic motion-aligned steering is shown in FIGS. 2B-D. In FIG. 2B, the user pushes the endoscope 220 in a distal direction, and the endoscope is computer-controlled to automatically articulate the second segment 234 to align the endoscope's motion with the camera's viewing axis. Thus, when the user pushes forward (in a distal direction) in FIG. 2B, the endoscope detects this motion and articulates the second segment 234 to compensate. The articulation of the second segment 234 may occur while the forward motion is occurring such that the active steering occurs when the endoscope 220 is in motion. The second segment 234 bends to align itself with the camera axis CA. This active steering causes the distal end of the endoscope 220 to bend upward toward the trachea 14, where the camera axis CA is pointing. In FIG. 2B, the field of view 230V is now pointed above the vocal cords 28, and both segments 232, 234 are bent upward (in an anterior direction, toward the patient's chest).

At this point, the user may steer the camera back down, to point the camera's view 230V at the vocal cords and into the trachea, as shown in FIG. 2C. For example, the user may tap on the vocal cords 28 on a touch screen display, and the endoscope responds by bending the first segment 232 downward to point toward the vocal cords 28. At this point, the first segment 232 is bent downward (in a posterior direction, toward the patient's back), while the second segment 234 is still bent upward (anterior), as shown in FIG. 2C.

From here, if the user pushes the endoscope 220 forward further into the patient (in a distal direction), the endoscope 220 will again actively steer itself to align its motion with the camera's axis CA, as shown in FIG. 2D. In FIG. 2D, the user has pushed the endoscope 220 forward through the vocal cords 28. The endoscope 220 detects forward motion and bends the second segment 234 in the anterior direction to align that motion with the camera's axis of view, CA. At this point both the segments 232, 234 are bent in the posterior direction, and the field of view 230V is now viewing the tracheal walls, past the vocal cords 28.

In an embodiment, the automatic motion-aligned steering is applied to both the first and second segments 232, 234. In this case, the system allows the user to steer the first segment 232 when the endoscope 220 is at rest or not in motion (to point the camera axis CA), and automatically steers both the first and second segments when the endoscope is moving. In another embodiment, the automatic motion-aligned steering allows the user to provide inputs to steer the first segment 232 even during motion, and the system interprets the user input as well as the motion signal to steer the first segment 232. That is, the system permits steering of the distal tip 29 via articulation of the first segment 232 and/or the second segment 234 during translation of the endoscope 220. In an embodiment, the user steering input is only used to directly steer the first segment 232 while the automatic or active steering is used to control both the segments 232, 234. That is, the user steering inputs cause direct movement of the first segment 232 to reorient the camera 230. When the camera 230 is in the desired orientation, the automatic steering controls the articulating of the segments 232,234 to maintain the camera field of view 230V along the camera axis CA during motion.

Figure 3:
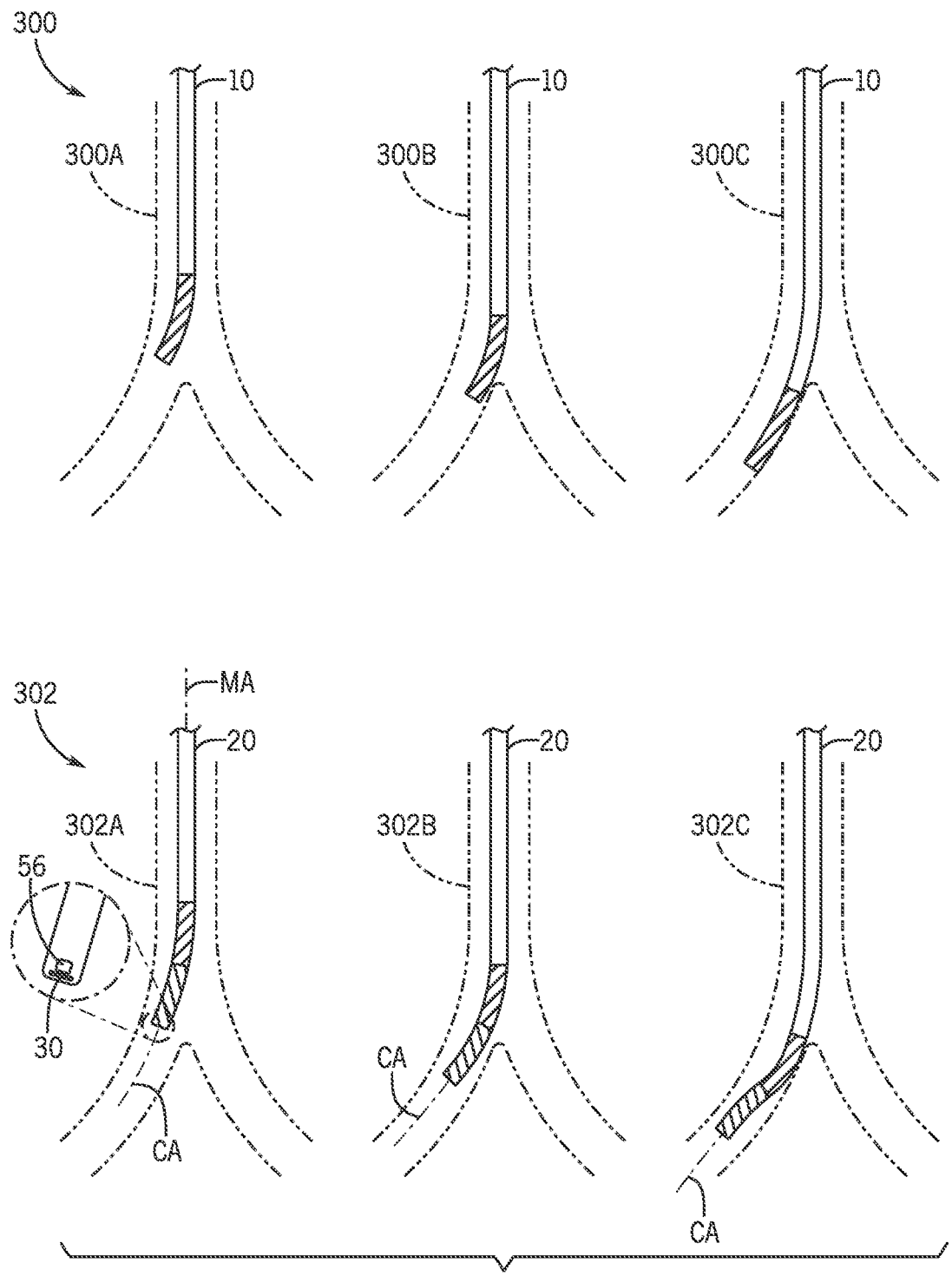
FIG. 3 is a cross-sectional view of two articulating endoscopes moving distally through patient tissue, to demonstrate the motion aligned steering in accordance with embodiments of the present disclosure.

FIG. 3 shows a schematic view of two different endoscopes moving through internal passages within a patient. In row 300, an endoscope 10 includes only one steerable segment at its distal end. The user can instruct the endoscope to steer this distal segment to point the endoscope and its camera where the user wants it to go (configuration 300A), but the endoscope is not able to actively align its motion with the camera's view by steering the single steerable segment at the distal end. As a result, when the user pushes the endoscope 10 forward (distally), the endoscope pushes and rubs along the patient's tissue (configurations 300B and 300C) as it moves forward. For example, when the endoscope is moving through bronchial passages in the lungs, the front leading edge of the endoscope 10 rubs up against the bronchial walls as it moves distally. This direct contact can irritate the tissue, as well as obscure the camera's view (by pointing it into the tissue or covering it with secretions). Here, the combination of single segment steering and translation of the endoscope 10 provides undesirable positioning of the endoscope 10.

In contrast, in row 302, an endoscope 20 according to an embodiment of the present disclosure includes two independently steerable segments at its distal end. In an embodiment, this endoscope 20 is computer-controlled to actively steer both segments to align distal motion of the endoscope with the camera's viewing axis. As a result, the endoscope 20 bends away from the tissue walls, reducing contact between the patient's tissue and the leading edge of the endoscope.

In an embodiment, the endoscope actively steers the two distal articulating segments to align its motion axis with its camera axis during forward (distal) motion of the endoscope, but not during rearward (proximal) motion of the endoscope. During rearward (proximal) motion, the user may steer the first (most distal) articulating segment to control the view of the camera, but the second articulating segment (proximal of the first) remains passive (not actively articulated).

Row 302 of FIG. 3 also shows an enlarged cut-away view of the distal end of the endoscope 20, to show the placement of the camera 30 and an orientation sensor 56. The example shows the camera 30 positioned at the terminus of the distal end of the endoscope 20, to obtain a clear view forward. The orientation sensor 56 is located just behind the camera 30. In an embodiment, the orientation sensor 56 is adjacent the camera 30. In an embodiment, the orientation sensor 56 is mounted on a printed circuit assembly (e.g., a flex circuit) behind the camera 30. In an embodiment, the orientation sensor 56 is mounted on the same printed circuit assembly as the camera 30, though the orientation sensor and the camera need not be in communication on the shared printed circuit assembly. In an embodiment, the orientation sensor has a size of between 1-2 mm in each dimension.

The orientation sensor 56 is an electronic component that senses the orientation (such as orientation relative to gravity) and/or movement (acceleration) of the distal end of the endoscope. The orientation sensor 56 generates a motion signal indicative of the orientation and/or movement. The orientation sensor 56 contains a sensor or a combination of sensors to accomplish this, such as accelerometers, magnetometers, and gyroscopes. The orientation sensor 56 may be an inertial measurement unit (IMU) or a magnetic, angular rate, and gravity (MARG) sensor that permits yaw measurement. The orientation sensor 56 detects static orientation and dynamic movement of the distal tip of the endoscope and provides a signal indicating a change in the endoscope's orientation and/or a motion of the endoscope. The orientation sensor 56 sends this signal to the controller. The orientation sensor 56 is located inside the tubular housing of the endoscope 20. As shown in FIG. 3, in an embodiment, the orientation sensor 56 is located very close to the terminus of the distal end of the endoscope 20, such as behind the camera 30, to enable the orientation sensor 56 to capture much of the full range of movement of the distal tip and camera 30. In an embodiment, the orientation sensor 56 is placed at a distal end of the first steerable portion, remote from the proximal end of the steerable portion, to place the orientation sensor away from the fulcrum of movement.

Row 302 of FIG. 3 also demonstrates how the articulation of the first and second segments can bring the motion axis into alignment with the camera axis. In a configuration 302A, the endoscope 20 is pointed toward a passage, as shown by the camera axis CA. The portion of the endoscope 20 shown is not contacting the side walls of the patient cavity or passage. If the user pushes forward to advance the endoscope 20, the endoscope 20 will move forward along a motion axis MA, which is offset from the camera axis CA. The controller detects this offset and responds by bending the distal segment or segments to compensate. For example, in configuration 302B, the endoscope 20 actively bends the second articulating segment to reduce the offset between the CA and the MA. By bending, the segment translates motion along the MA into motion along the CA. As the user continues to advance the endoscope 20 forward, it eventually comes into contact with the patient tissue, as shown in configuration 302C. The contact point with the tissue deflects the endoscope 20 in the desired direction, so that additional pushing by the user will move the endoscope forward along camera axis CA. Thus, the remainder of the endoscope 20 does not need to be actively steerable. The remainder of the scope (proximal of the two articulating segments) should be flexible so that it can passively follow the articulating segments, curving to follow a tortuous path along the passages through which the articulating segments steered.

The articulation of the first articulating segment and the second articulating segment may be in parallel (i.e., at the same time) or may be performed in series or in an alternating (e.g., rapidly alternating) manner. In an example, the articulation alternates by driving one motor at a time in quick succession. Further, the articulation of the first articulating segment and the second articulating segment may be in opposing directions such that one segment countersteers from the direction of the other segment.

Row 302 of FIG. 3 also demonstrates the shallow angle of contact between the second steerable segment and the patient's tissue. In an embodiment, the second segment has a length that is long enough to lift the first segment off the tissue walls with a shallow angle of contact between the second segment and the tissue. In an embodiment, that angle of contact is about 40 degrees or less. Thus the second segment has enough length to advance the first segment away from the patient's tissue without the second segment having to bend more than about 40 degrees. In an embodiment, the angle is about 50 degrees or less, or about 30 degree or less. The shallow angle also helps to protect the patient's tissue, reducing irritation by creating a smooth curve rather than a sharper curve. The shallow angle also enables the endoscope to glide across the tissue with less force from the user. In an embodiment, the second segment is longer than the first segment. In an embodiment, the first segment has a length of about 35 mm, and the second segment has a length of about 50 mm. In an embodiment, the first segment has a length of about 20-40 mm, and the second segment has a longer length in the range of about 30-50 mm.

In an embodiment, the endoscope uses the signal from the orientation sensor 56 to identify the direction of gravity (downward), and then bends the second segment upward in the opposite direction (opposite gravity) to lift the first segment and the camera up of the patient's tissue. The direction of gravity may also be used as an input to determine proximity to particular portions of the patient's tissue. If the endoscope is pushing against the tissue, the location of the push point or fulcrum may be identified in absolute space. Location info can be used to scale the sensitivity to user inputs. The further into the airway, the smaller the structures get. If relative location of nearby structures is being inferred, it can help scale back so similar input gestures produce similar movements in the video feed as one moves along. Similarly, if all reference points are far away, more exaggerated articulations are generated from relatively similar input.

Figure 4:
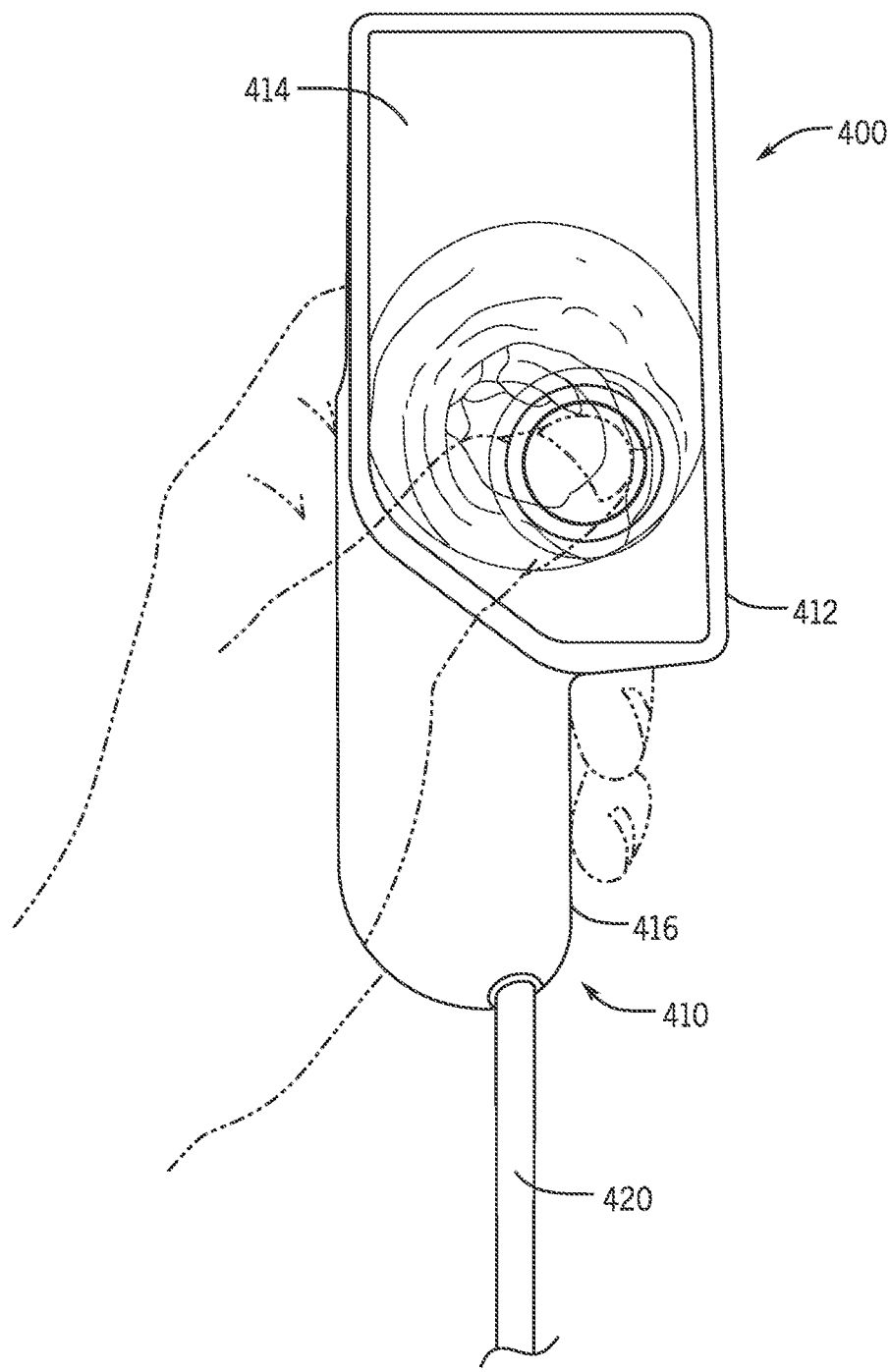
FIG. 4 is a front view of a graphical user interface, according to embodiments of the present disclosure.

FIG. 4 is a front view of a graphical user interface (GUI) 400, according to embodiments of the present disclosure. The GUI 400 is presented on a display screen 412 of a controller 410, which in FIG. 4 is a hand-held wand 416. In this embodiment, the display screen 412 includes a touch screen 414. The GUI 400 receives user inputs by detecting the user's touch on the screen 414. The user touches the screen to indicate where the user wants to point the camera (such as camera 230 of endoscope 220). The GUI 400 sends this touch input to a processor (described more fully below), which generates instructions to bend the first distal segment (such as segment 232) to point the camera axis in the direction that the user touched. In this particular example, the user can hold the wand 416 with his or her left hand, and touch the screen 414 with a thumb of that left hand, leaving the right hand free to hold and advance the endoscope. The user can steer the endoscope camera (such as camera 230) by tapping the screen 414 with his or her thumb (as shown in FIG. 4), and then can advance the endoscope 420 by pushing it forward (or remove the endoscope 420 by pulling back) with his or her right hand.

The controller 410 is shown as a wand 416, and the endoscope 420 is removably connected directly to the wand 416, for passage of control signals from the wand to the endoscope and video signals from the endoscope to the wand. In other embodiments the controller 410 may have other forms or structures. For example, the controller 410 may be a video laryngoscope, table-top display screen, tablet, laptop, puck, or other form factor.

In an embodiment, the GUI 400 includes a touch screen that is responsive to taps, touches, or proximity gestures from the user. For example, the user may enter a touch gesture (such as a tap, double-tap, tap-and-hold, slide, highlight, or swipe) to identify a target point or direction within the image on the screen. This gesture identifies where the user desires to steer the endoscope, and the controller translates this into a real world steering direction and corresponding instructions for operating the steering system to move the distal steerable segment of the endoscope in that direction. The user may swipe in a desired direction on the touch screen 414 to reorient the distal end of the endoscope. A desired orientation or movement of the camera may be interpreted from the direction and length of the swipe movement on the touch screen 414. In an embodiment, the steering input may additionally or alternatively be provided via user selection from a menu, selection of soft keys, pressing of buttons, operating of a joystick, etc. In an embodiment, a user may circle or otherwise highlight the portion of the displayed image towards which the distal end should be steered.

The controller 410 with the endoscope 420 operates as a two-part endoscope, where the controller 410 serves as the handle, display, and user input for the endoscope 420. In an embodiment, the controller 410 is reusable and the endoscope 420 is single-use and disposable, to prevent cross-contamination between patients or caregivers. The controller 410 itself does not need to come into contact with the patient, and it can be wiped and cleaned and ready to use for the next patient, with a new sterile endoscope 420.

In an embodiment, the endoscope 420 (e.g., endoscope 220, see FIG. 2) actively articulates both the first and second segments (e.g., segments 232, 234, see FIG. 2, or, alternatively, just the second segment 234) automatically in response to detected motion, without steering input from the user. The user provides two inputs, which are the direction of the camera axis CA (which the user can input by tapping on the screen 414 in FIG. 4), and translation of the endoscope proximally or distally. The user does not need to provide additional input to steer the segments 232, 234 in the direction the user wishes to go. Rather, the endoscope 220 will steer itself automatically to attempt to align its motion with the camera axis. This automatic steering frees the user to focus on the anatomy displayed on the screen 414 (in FIG. 4) and where the user wants to go, without having to determine how to manually manipulate the endoscope to move in that direction.

Figure 5C:
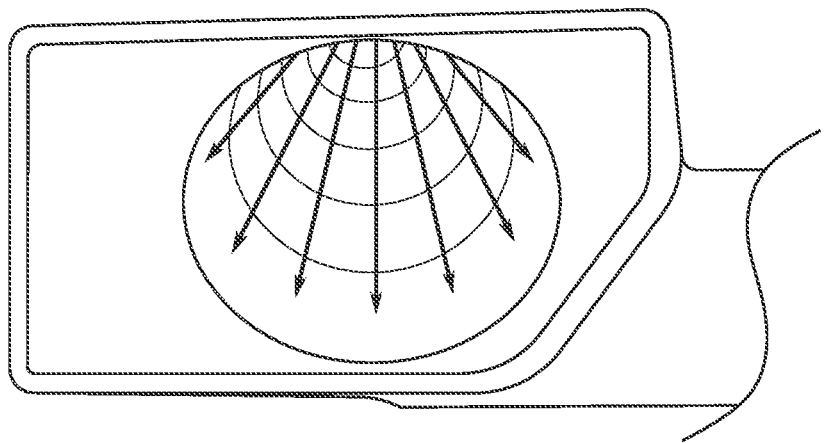
FIG. 5C is a schematic illustration of optical flow techniques for motion alignment, according to embodiments of the present disclosure.
Figure 5B:
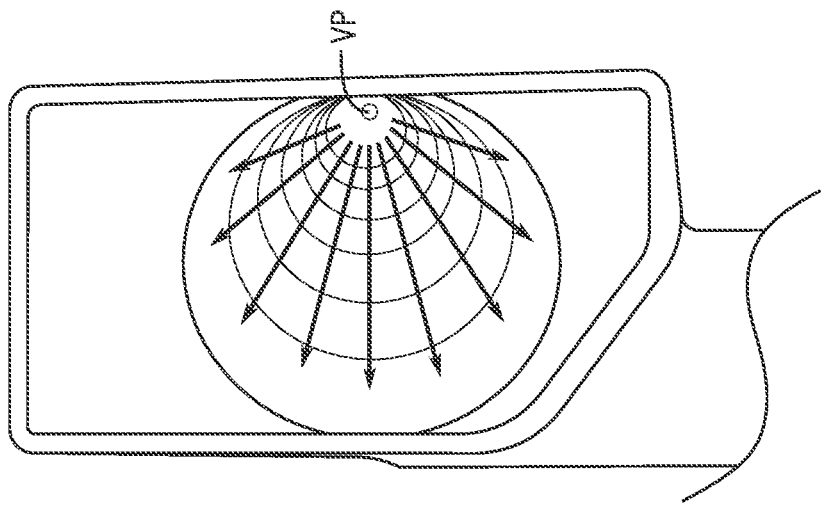
FIG. 5B is a schematic illustration of optical flow techniques for motion alignment, according to embodiments of the present disclosure.
Figure 5A:
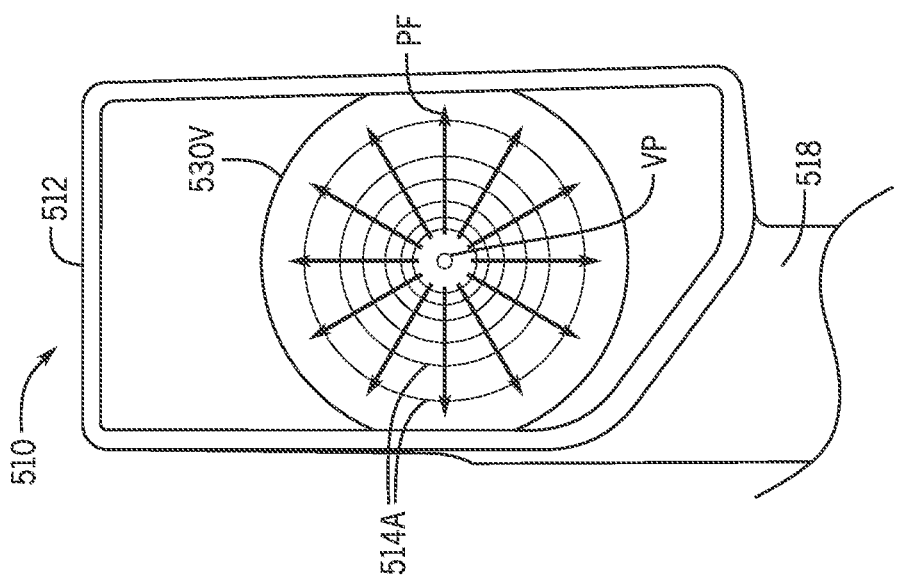
FIG. 5A is a schematic illustration of optical flow techniques for motion alignment, according to embodiments of the present disclosure.

The steering control system may use computer vision techniques to identify changes in the camera orientation and/or to predict a desired user navigation direction. FIGS. 5A-C are schematic illustrations of optical flow techniques for motion alignment, according to embodiments of the present disclosure. This figure gives an example approach for aligning motion with the camera axis. FIG. 5A-C show views from an endoscope camera, displayed on a display screen 512 of a controller 510, which in this case is a video laryngoscope 518. The display screen 512 shows the field of view 530V from an endoscope camera inside a patient cavity. In FIG. 5A, the field of view 530V is pointed along a patient's trachea, and the view includes sequential tracheal rings 514A.

The diverging arrows PF represent the flow of pixels across the screen when the endoscope moves forward into the trachea. As the endoscope moves forward, individual objects within the view will move along these arrows. As a result, the arrows PF indicate the direction the objects in the image move as the endoscope is advanced by those objects. In particular, the axis of motion of the endoscope is toward the point from which these objects appear to diverge. This point may also be referred to as the vanishing point VP, which is the point of from which the arrows PF diverge. When the objects in the image appear to move along the arrows PF, the endoscope is moving toward the point VP.

In FIG. 5A, the vanishing point VP is near the center of the field of view 530V. This indicates good alignment between the motion axis and the camera axis. That is, the camera's field of view is pointed at the vanishing point, which is the intended direction of the endoscope's movement.

In FIG. 5B, the vanishing point VP is offset to the right side of the camera's field of view 530V. This view can result when the camera steers to the left (in the orientation of FIG. 5), while the endoscope continues to move in the direction it was previously pointed. The flow of objects (along arrows PF) is now becoming more parallel, rather than diverging from the center of the view.

In FIG. 5C, the vanishing point VP is out of view. This view can result when the camera steers further to the left (in the orientation of FIG. 5A-C). The arrows PF are becoming even more parallel, rather than diverging. This view indicates that the motion axis and camera axis are not aligned.

An analysis of pixel flow, vanishing point, or pixel divergence can be used to actively control an endoscope to improve motion and camera alignment. A group of pixels may be identified as an object in an image, and the pixel flow may refer to movement of the object to different pixels of the camera/display. In an embodiment, an endoscope controller performs an automated analysis to generate an alignment metric indicating a degree of alignment between a camera axis and a motion axis of the endoscope. The controller generates a steering signal to articulate the first and/or second articulating segments of the endoscope to improve the alignment metric.

In an embodiment, pixel characteristics, such as pixel brightness, pixel speed, and pixel depth may be used to track motion. For example, pixel brightness may be used to estimate closeness to the camera (with brightness indicating proximity—that is, brighter pixels are more likely to be closer to the camera than less bright pixels, which are likely to be farther away), and changes in pixel brightness during motion may be used to track local changes in camera orientation.

In an embodiment, the alignment metric is a deviation of an object (in the field of view) from a center of the field of view. The controller identifies an object (such as the vocal cords, a bronchial passage, a tumor, or other point of anatomy) near the center of the field of view and tracks that object within the field of view. If the object remains near the center, the endoscope is likely to be moving in the direction it is pointed. If the object deviates from the center, the endoscope may no longer be moving in that direction, and the controller articulates the endoscope to compensate. In this manner, the camera axis may be locked onto a particular anatomical feature via active steering. In an embodiment, the controller identifies passage walls (tissue) in the image data and automatically steers the camera axis to be positioned in the middle of the passage (pointed between walls, not directly at a wall) and pointed in the direction of forward motion down the passage.

In an embodiment, the alignment metric is a degree of spread (divergence) of pixels moving within a field of view.

In an embodiment, the alignment metric is a percent convergence of optical flow lines in a field of view.

In an embodiment, the alignment metric is a proximity of a point in the field of view to a center of the field of view. This proximity is an indicator of whether the endoscope is moving toward that point. In an embodiment, the point is a vanishing point (of pixels moving in the field of view), and proximity of the vanishing point to the center indicates whether the endoscope is moving in the direction the camera is pointed. In another embodiment, the point is a likely target (such as an anatomical feature) within the field of view, and the proximity of the target to the center indicates whether the endoscope is moving toward the target. An anatomical target can also be used in a negative feedback loop, to calculate error and adjust—for example, if the target moves away from the center of view, then the system steers the endoscope in the opposite direction.

In an embodiment, the alignment metric is an amount of agreement or discrepancy between the orientation of the distal end of the endoscope and motion of the endoscope. These two signals—orientation and acceleration—can be obtained from the orientation sensor. If the endoscope is moving where the camera is pointed, then the orientation and acceleration signals will align.

In an embodiment, the controller uses local and global orientation information of the endoscope to maintain the camera axis in a desired orientation during motion of the endoscope and navigation within the passageways of the patient. The local orientation may be at least in part extracted from image data captured by the camera. The local orientation may include identifying the presence and location of anatomical features and determining the position and orientation of the camera relative to the anatomical features. The global information may be extracted from the motion signal from the orientation sensor, and may include the orientation of the endoscope relative to gravity and the motion of the endoscope caused by patient motion or user manipulation. In combination, the local and global information may be used to provide steering control instructions to steer the first articulating segment and/or the second articulating segment.

Figure 6:
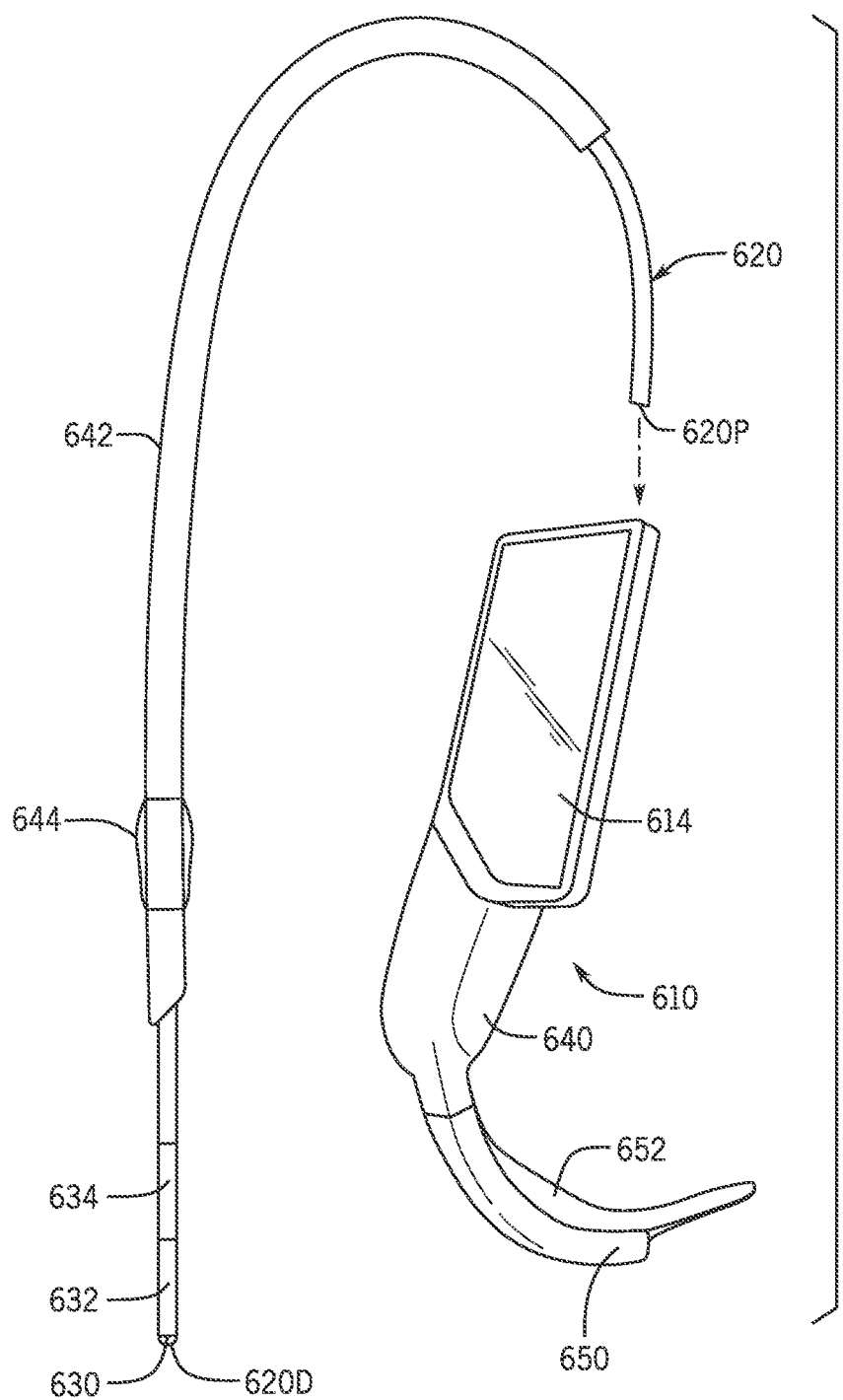
FIG. 6 is a perspective view of a controller and endoscope, according to embodiments of the present disclosure.

FIG. 6 shows a perspective view of a controller 610 including a handle or grip 640 and screen 614. In an embodiment, the controller 610 is a laryngoscope having a camera 650 and coupled to a laryngoscope blade 652. The controller 610 connects to an endoscope 620 which is fed through an endotracheal tube 642 (with an inflatable cuff 644). The endoscope 620 is connected at its proximal end 620P to the controller 610. At its opposite distal end 620D, the endoscope includes two articulating segments 632, 634 and a camera 630. In one example use case, the controller 610 and endoscope 620 are used during an intubation procedure of a patient. The proximal end 620P of the endoscope is connected to the controller, and images from the camera 630 are displayed on the screen 614. With one hand (such as the left hand), the user taps on the screen 614 to steer the endoscope camera 630, and with the other hand (such as the right hand), the user pushes the endoscope 620 forward into the patient cavity. When the endoscope is in place (for an intubation, the endoscope is passed through the patient's vocal cords into the trachea), the proximal end 620P is disconnected from the controller 610 and the endotracheal tube 642 passed over the endoscope. Once the proximal end 620P emerges from the endotracheal tube 642, the endoscope can be reconnected to the controller 610. The endotracheal tube 642 is then passed over the endoscope into the trachea, and then the endoscope can be withdrawn from the patient, retracting it back through the tube 642.

In an embodiment the disclosed endoscope steering techniques may be used as part of an awake intubation in which the user faces the patient, and the patient may be sitting upright. The endoscope 620 may essentially "flip" over from a first direction (where the patient's chest is down on the user's screen) (at the start, when the endoscope 620 is being fed into the patient's nose) to a second opposite orientation (where the patient's chest is up on the user's screen) (after the endoscope 620 has passed through the nasal passage). By allowing the user to orient the camera to particular features of the captured image, the camera axis is maintained via automatic steering that is performed in the background by the controller 610 and without user input.

Each articulating segment at the distal end of the endoscope is manipulated by a steering system, which operates an actuator that is coupled to the segment to bend or straighten the segment. The steering system may include one or more memory metal components (e.g., memory wire, Nitinol wire) that changes shape based on electrical input, a piezoelectric actuators (such as the SQUIGGLE motor from New Scale Technologies, Victor N.Y.), a retractable sheath (retractable to release a pre-formed curved component such as spring steel which regains its curved shape when released from the sheath), mechanical control wires (pull wires), hydraulic actuators, servo motors, or other means for bending, rotating, or turning the distal end or components at the distal end of the endoscope.

Complex motion patterns can be achieved with actuators coupled to two independent articulating segments at the distal end of the endoscope. For example, an "S" shape can result when the two segments are actuated in different directions (such as one curves up and the other curves down). The endoscope includes a housing that is flexible to permit manipulation of the endoscope within the patient cavity.

Further, because articulation of the segments can change rotational orientation of the distal end, distal bending and movement of the endoscope is accomplished independent of the orientation, position, or movement of the proximal end of the endoscope. Accordingly, the structure of the endoscope may be less torsionally stiff relative to implementations in which the steering relies on torsional force transfer. In an embodiment the endoscope is an extruded structure with low torsional stiffness (low enough that torsional rotation does not translate from the proximal to the distal end). In an embodiment, the endoscope is a non-braided structure, such as an extruded polymer. In an embodiment, the endoscope is an extruded structure devoid of torsional stiffeners such as braided wires or braided structures.

Figure 7:
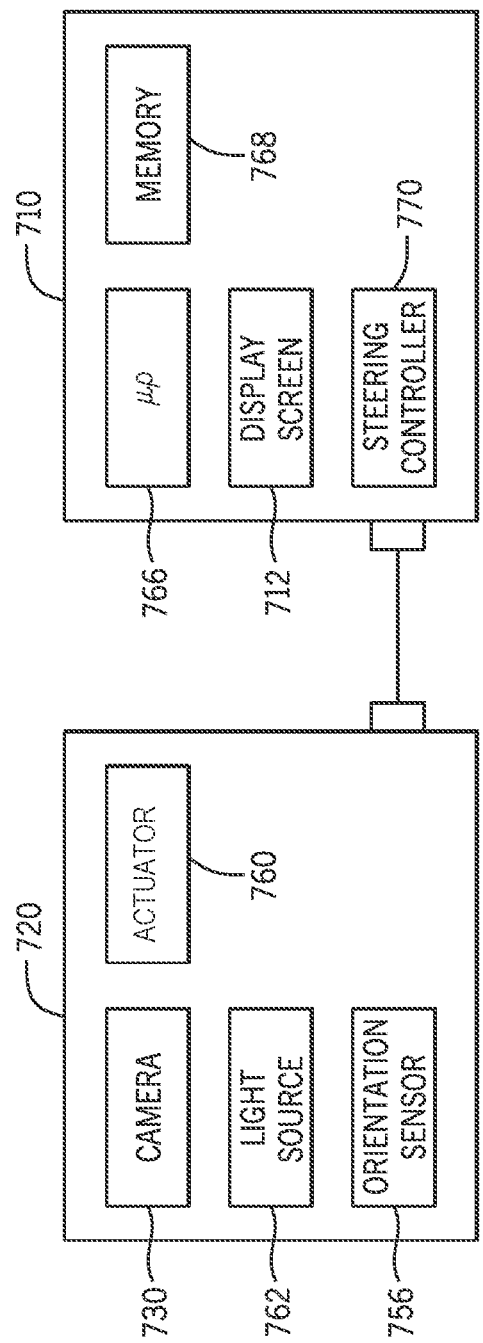
FIG. 7 is a block diagram of a controller and endoscope, according to embodiments of the present disclosure.

A block diagram is shown in FIG. 7, including an endoscope 720 and a controller 710. The connection between them may be wired (in which case they each have an electrical connector) or wireless (in which case they each include a wireless transceiver). The endoscope 720 includes a camera 730 and an orientation sensor 756 at the distal end of the endoscope. The orientation sensor may be an inertial measurement unit (INIU), accelerometer, gyroscope, or other suitable sensor. The endoscope 720 also includes a light source 762 and an actuator 760 that is coupled to the distal steerable segments, to bend or un-bend them, as described herein.

The controller 710 includes a processor 766 or chip (such as a chip, a processing chip, a processing board, a chipset, a microprocessor, or similar devices), a hardware memory 768, a display screen 712 (such as a touch screen), and a steering control system 770, which may include a motor or other driver for operating the actuator. The controller 710 may also include some other type of user input (buttons, switches), and a power source (such as an on-board removable and/or rechargeable battery).

The controller 710 may also include a power source (e.g., an integral or removable battery) that provides power to one or more components of the endoscope as well as communications circuitry to facilitate wired or wireless communication with other devices. In one embodiment, the communications circuitry may include a transceiver that facilitates handshake communications with remote medical devices or full-screen monitors. The communications circuitry may provide the received images to additional monitors in real time.

Figure 8:
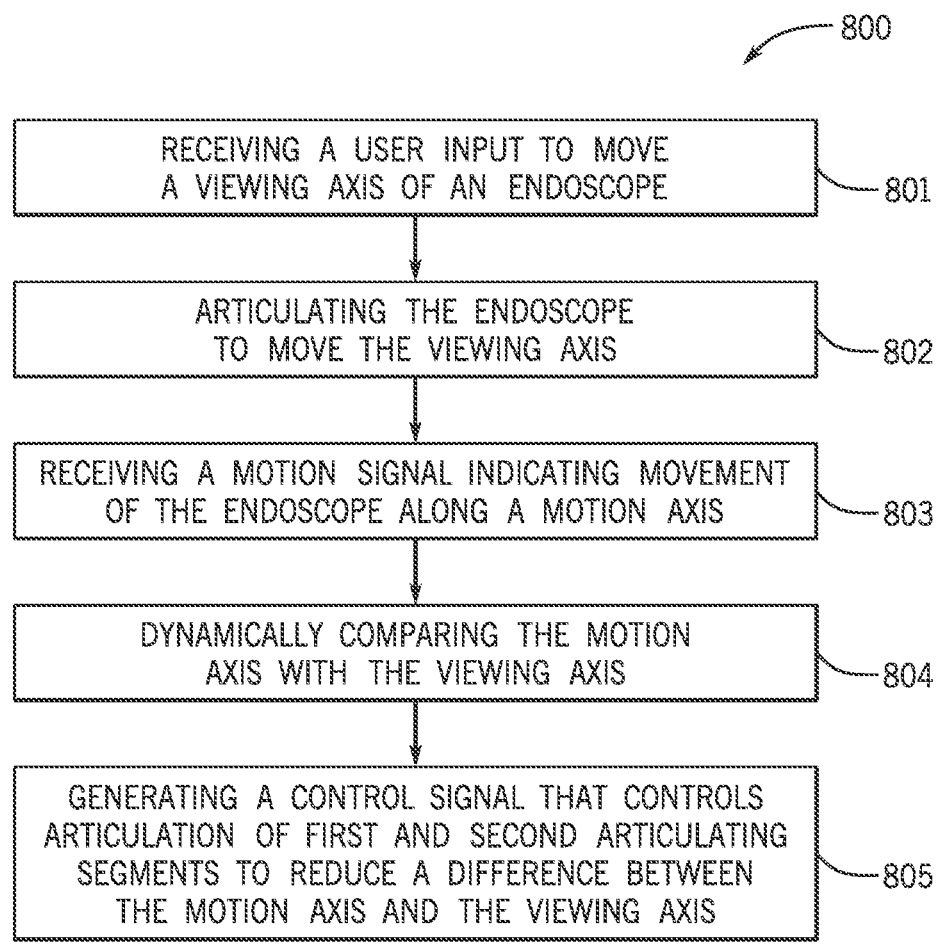
FIG. 8 is a flowchart depicting a method for computer-aided steering of an endoscope, according to embodiments of the present disclosure.

FIG. 8 is a flowchart depicting a method 800 for computer-aided steering of an endoscope, according to an embodiment. The method includes receiving a user input to move a viewing axis of an endoscope (801), and in response to the user input, articulating the endoscope (such as the first distal articulating segment) to move the viewing axis (802). The method also includes receiving a motion signal indicating movement of the endoscope along a motion axis (803), such as a motion signal from an orientation sensor, and dynamically comparing the motion axis with the viewing axis (804). In an embodiment, comparing the motion axis with the viewing axis includes generating an alignment metric indicating a degree of alignment between the two axes. The method also includes generating a control signal that controls articulation of first and second articulating segments to reduce a difference between the motion axis and the viewing axis (805). The control signal includes instructions for articulating the first and second segments to improve the alignment metric. These steps may be performed by a processor or chip as part of a controller for the endoscope.

Figure 9:
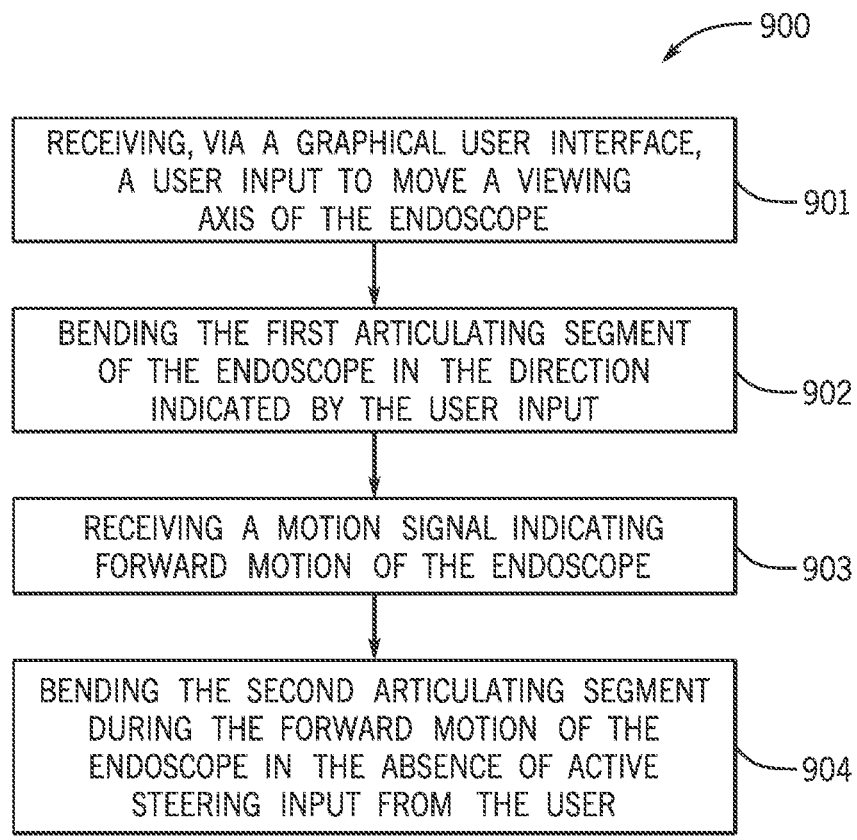
FIG. 9 is a flowchart depicting a method for computer-aided steering of an endoscope, according to embodiments of the present disclosure.

FIG. 9 is a flowchart depicting a method (900) for computer-aided steering of an endoscope, according to an embodiment. The method includes receiving, via a graphical user interface, a user input to move a field of view of the endoscope (901), and articulating the first articulating segment of the endoscope to move the field of view in the direction indicated by the user input (902). Thereafter, the method includes receiving a motion signal indicating forward motion of the endoscope (903), and actively steering the second articulating segment during the forward motion of the endoscope in the absence of user steering input from the user (904). The active steering is accomplished by the controller that generates a steering signal to steer the second articulating segment, based on a comparison of the direction of motion and the direction of the field of view, as described above. As the user pushes and advances the endoscope forward within the patient cavity, the controller automatically steers the first and/or second articulating segments to align the motion direction with the viewing direction. This active steering is done without any further steering input from the user; at this point the user may simply advance the endoscope forward, and the controller will automatically steer the first and/or second articulating segments. This automatic steering, without steering input from the user, enables the user to focus on the view from the camera of the endoscope and the movement of the endoscope forward, without having to simultaneously work to manually steer the articulating sections of the endoscope.

Based on this approach, the user's input is limited to pointing the camera and advancing the endoscope—not bending the articulating segments to navigate them through the patient's anatomy. By pointing the camera where the user wants to go and then advancing the endoscope forward, the controller will automatically bend the first and second articulating segments to align the motion axis with the direction the user wants to go. The controller bends these segments to behave as a virtual gimbal behind the camera, swiveling the endoscope behind the camera to keep the endoscope moving in the direction that the camera is pointed. In this manner, the user is prompted to provide more intuitive inputs that generally indicate desired direction of the camera while controlling forward motions of the endoscope. The user provides rough steering guidance, e.g., via the touch screen, and the controller generates the instructions for fine or more precise steering control based on the rough guidance. Further, based on the user's steering input or steering that is locked onto a particular anatomic feature, the controller may predict or estimate the future steering instructions. For example, based on the absolute or relative location of the distal end in the patient and/or identified features in the image, a desired orientation within the passage can be predicted. This prediction or interpretation of user intent can be used to maintain the desired orientation of the camera's field of view, e.g., in the center of the passageway or keeping the anatomical feature in the center of the passageway. A user's forward steering motion at the proximal end of the endoscope may vary from user to user based on their preferences. However, the controller corrects for these variations by automatically steering based on the desired orientation of the camera axis and to maintain the desired orientation, which corrects for user variations in manipulation style of the proximal end of endoscope. Given an image in which only local information is relevant to the user and global info from the orientation sensor is hidden to the user, the algorithm will either look for specific features or potential destinations. From user touch coordinates, the speed and magnitude of gestures can indicate which of the potential targets the user is aiming for, e.g., using filtering or a long short-term memory (LSTM network). For the case where a user's thumb stays on the screen, gestures will be parsed out from the time series.

Further, in addition to accounting for movement of the endoscope as manipulated by the user, the present techniques also provide corrections or adjustments for patent movement during operation of the endoscope. During certain procedures, the patent may move independently or be repositioned by a caregiver, e.g., the patient may sit up, roll over, etc. These patient movements are reflected in the motion signal from the orientation sensor, which may provide orientation of the endoscope relative to gravity or an absolute orientation. Changes in absolute orientation may be analyzed with respect to the desired camera axis such that the controller automatically adjusts the position of the camera to account for patient movement to return the camera axis to its desired orientation. In one example, an endoscope in use in a patient positioned on their back in which the anterior side of the patient corresponds to the absolute up position and the posterior side corresponds to a gravitational down position. In this orientation the camera is also oriented in the direction of gravity and absolute orientation for the caregiver. In cases in which this patient is flipped over to be positioned on the patient's side or stomach, the controller may reorient the image and/or indicate these changes in orientation relative to gravity via the graphical user interface to show that the frame of reference of the camera is rotated from the original orientation and may translate the steering commands from the frame of reference of the camera axis into the frame of reference of the endoscope. In this manner, the anatomy is presented in a familiar way for the user. In an embodiment, the user may toggle between gravity orientation and patient orientation. If the endoscope is in the patient during the rotation, the orientation signal and camera feed can be reconciled to indicate that the patient is being repositioned. If the patient is already positioned non-supine when the endoscope is introduced, the image may be reoriented.

The processor (e.g., processor 766, see FIG. 7) may include one or more application specific integrated circuits (ASICs), one or more general purpose processors, one or more controllers, FPGA, GPU, TPU, one or more programmable circuits, or any combination thereof. For example, the processor may also include or refer to control circuitry for the display screen. The memory may include volatile memory, such as random access memory (RAM), and/or non-volatile memory, such as read-only memory (ROM). The image data captured by the endoscope camera and/or the laryngoscope camera (if present) may be stored in the memory, and/or may be directly provided to the processor. Further, the image data for each patient procedure may be stored and collected for later review. The memory (e.g., hardware memory 768, see FIG. 7) may include stored instructions, code, logic, and/or algorithms that may be read and executed by the processor to perform the techniques disclosed herein.

While the present techniques are discussed in the context of endotracheal intubation, it should be understood that the disclosed techniques may also be useful in other types of airway management or clinical procedures. For example, the disclosed techniques may be used in conjunction with placement of other devices within the airway, secretion removal from an airway, arthroscopic surgery, bronchial visualization past the vocal cords (bronchoscopy), tube exchange, lung biopsy, nasal or nasotracheal intubation, etc. In certain embodiments, the disclosed visualization instruments may be used for visualization of anatomy (such as the pharynx, larynx, trachea, bronchial tubes, stomach, esophagus, upper and lower airway, ear-nose throat, vocal cords), or biopsy of tumors, masses or tissues. The disclosed visualization instruments may also be used for or in conjunction with suctioning, drug delivery, ablation, or other treatments of visualized tissue and may also be used in conjunction with endoscopes, bougies, introducers, scopes, or probes.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A method for computer-aided steering of an endoscope, comprising:

receiving, via a touch screen display, a user input to move a viewing axis of an endoscope, the endoscope comprising:
  a first articulating segment positioned at a distal end of the endoscope;
  a second independently articulating segment located at the distal end of the endoscope and coupled to a proximal end of the first articulating segment;
  a camera, positioned at the distal end of the first articulating segment, having a field of view along the viewing axis; and
  an orientation sensor positioned at the distal end of the endoscope;
in response to the user input, articulating the first articulating segment of the endoscope to move the viewing axis;
receiving from the orientation sensor a motion signal indicating movement of the endoscope along a motion axis;
comparing, at a processing chip, the motion axis with the viewing axis, wherein comparing the motion axis with the viewing axis comprises generating an alignment metric indicating a degree of alignment between the camera axis and the motion axis; and
generating a steering signal that controls articulation of the first and second articulating segments to reduce a difference between the motion axis and the viewing axis.

2. The method of claim 1, further comprising identifying an object near a center of the field of view and tracking movement of the object within the field of view, and wherein the alignment metric comprises a deviation of the object from the center of the field of view.

3. The method of claim 1, wherein the alignment metric comprises a degree of spread of pixels moving in the field of view.

4. The method of claim 1, wherein the alignment metric comprises a degree of convergence or divergence of optical flow lines in the field of view.

5. The method of claim 1, wherein the alignment metric comprises a proximity of a vanishing point in the field of view with a center of the field of view.

6. The method of claim 1, comprising articulating the first articulating segment, the second articulating segment, or a combination thereof in response to the steering signal.

7. The method of claim 6, comprising articulating the second articulating segment and the first articulating segment in opposing directions.

8. The method of claim 1, wherein the second articulating segment has a length longer than the first articulating segment.

9. The method of claim 8, wherein the first articulating segment has a length of about 20-40 mm and the second articulating segment has a length of about 30-50 mm.

10. The method of claim 1, wherein the steering signal is generated during forward motion of the endoscope.

11. The method of claim 1, wherein the user input comprises a direction of the viewing axis and translation of the endoscope forward or rearward.

12. The method of claim 1, wherein the generated steering signal causes the viewing axis to be positioned in the middle of a passage and pointed in the direction of forward motion down the passage.

13. The method of claim 1, further steering signal causes the viewing axis to be maintained in a desired orientation during motion of the endoscope and navigation within the passageway.

* * * * *